US008532368B2

(12) United States Patent
Se et al.

(10) Patent No.: US 8,532,368 B2
(45) Date of Patent: *Sep. 10, 2013

(54) METHOD AND APPARATUS FOR PRODUCING 3D MODEL OF AN ENVIRONMENT

(75) Inventors: Shuen Yan Stephen Se, Richmond (CA); Piotr Jasiobedzki, Mississauga (CA)

(73) Assignee: MacDonald Dettwiler and Associates Inc., Brampton, ON (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/210,275

(22) Filed: Aug. 15, 2011

(65) Prior Publication Data
US 2012/0120072 A1    May 17, 2012

Related U.S. Application Data

(60) Continuation of application No. 12/654,451, filed on Dec. 18, 2009, now Pat. No. 8,031,909, which is a division of application No. 11/352,399, filed on Feb. 13, 2006, now Pat. No. 7,860,301.

(60) Provisional application No. 60/651,639, filed on Feb. 11, 2005.

(51) Int. Cl.
*G06K 9/00* (2006.01)

(52) U.S. Cl.
USPC ............ 382/154; 382/254; 382/260; 382/284

(58) Field of Classification Search
USPC ............. 382/154, 219; 701/28, 16; 345/420, 345/43
See application file for complete search history.

(56) References Cited

U.S. PATENT DOCUMENTS 4,991,095 A    2/1991  Swanson
5,267,042 A *  11/1993  Tsuchiya et al. .............. 348/239
(Continued)

OTHER PUBLICATIONS

Huber et al., "3D Modeling Using a Statistical Sensor Model and Stochastic Search", Proceedings of the 2003 IEEE Computer Society Conference on Computer Vision and Pattern Recognition, Jun. 18-20, 2003, vol. 1, p. 858-865.

*Primary Examiner* — Vu Le
*Assistant Examiner* — Aklilu Woldemariam
(74) *Attorney, Agent, or Firm* — Lynn C. Schumacher; Hill & Schumacher

(57) ABSTRACT

The present invention provides a system (method and apparatus) for creating photorealistic 3D models of environments and/or objects from a plurality of stereo images obtained from a mobile stereo camera and optional monocular cameras. The cameras may be handheld, mounted on a mobile platform, manipulator or a positioning device. The system automatically detects and tracks features in image sequences and self-references the stereo camera in 6 degrees of freedom by matching the features to a database to track the camera motion, while building the database simultaneously. A motion estimate may be also provided from external sensors and fused with the motion computed from the images. Individual stereo pairs are processed to compute dense 3D data representing the scene and are transformed, using the estimated camera motion, into a common reference and fused together. The resulting 3D data is represented as point clouds, surfaces, or volumes. The present invention also provides a system (method and apparatus) for enhancing 3D models of environments or objects by registering information from additional sensors to improve model fidelity or to augment it with supplementary information by using a light pattern projector. The present invention also provides a system (method and apparatus) for generating photo-realistic 3D models of underground environments such as tunnels, mines, voids and caves, including automatic registration of the 3D models with pre-existing underground maps.

33 Claims, 9 Drawing Sheets

(56) References Cited

U.S. PATENT DOCUMENTS

| | | | |
|---|---|---|---|
| 5,365,597 A * | 11/1994 | Holeva | 382/318 |
| 5,566,246 A * | 10/1996 | Rao | 382/154 |
| 5,668,595 A * | 9/1997 | Katayama et al. | 348/218.1 |
| 5,699,444 A * | 12/1997 | Palm | 382/106 |
| 6,009,359 A | 12/1999 | El-Hakim | |
| 6,351,573 B1 * | 2/2002 | Schneider | 382/294 |
| 6,507,665 B1 * | 1/2003 | Cahill et al. | 382/154 |
| 6,516,099 B1 * | 2/2003 | Davison et al. | 382/284 |
| 6,711,293 B1 | 3/2004 | Lowe | |
| 6,781,618 B2 | 8/2004 | Beardsley | |
| 7,003,134 B1 * | 2/2006 | Covell et al. | 382/103 |
| 7,184,088 B1 * | 2/2007 | Ball | 348/348 |
| 7,254,265 B2 * | 8/2007 | Naske et al. | 382/154 |
| 7,466,336 B2 * | 12/2008 | Regan et al. | 348/50 |
| 7,804,530 B2 * | 9/2010 | Pryor | 348/239 |
| 2001/0010546 A1 * | 8/2001 | Chen | 348/218 |
| 2005/0265583 A1 * | 12/2005 | Covell et al. | 382/103 |
| 2006/0158522 A1 * | 7/2006 | Pryor | 348/207.99 |
| 2007/0140580 A1 * | 6/2007 | Heath et al. | 382/260 |

* cited by examiner

METHOD AND APPARATUS FOR PRODUCING 3D MODEL OF AN ENVIRONMENT

CROSS REFERENCE TO RELATED U.S. PATENT APPLICATIONS

This patent application is a Continuation application of utility patent application Ser. No. 12/654,451, entitled METHOD AND APPARATUS FOR PRODUCING 3D MODEL OF AN UNDERGROUND ENVIRONMENT, which is a Divisional application of U.S. patent application Ser. No. 11/352,399 entitled 3D IMAGING SYSTEM, which claims priority benefit from U.S. Provisional patent application Ser. No. 60/651,639 filed on Feb. 11, 2005 entitled 3D IMAGING SYSTEM, filed in English, which is incorporated herein in its entirety by reference.

FIELD OF THE INVENTION

The present invention is related to an apparatus and a method for creating three-dimensional (3D) computer models (represented, for example, as point clouds, surfaces, or volumes) of environments and/or objects from a plurality of images from stereo and monocular cameras.

BACKGROUND OF THE INVENTION

Creation of photo-realistic and non photo-realistic three-dimensional (3D) calibrated models of observed scenes and objects has been an active research topic for many years and many commercial systems exist. Such 3D models can be used for visualization, virtual presence, operations planning and rehearsal, training and measurements. They are useful for many applications including planetary rover exploration, autonomous vehicle guidance, navigation and operation, industrial automation and robotics, forensics, mining, geology, archaeology, real estate, virtual reality, computer games, etc.

Existing systems use sensors and techniques such as rangefinders (scanning and non-scanning), and stereo and monocular camera images to obtain 3D data. As data sets obtained from one sensor location do not show the complete object/environment surface due to insufficient field of view, depth of field or resolution of the sensor and/or visibility, it is necessary to move the sensor into another location to acquire another 3D view.

Multiple 3D data sets obtained from different sensors positions may be registered together to form one complete model using either external systems or by selecting and matching features observed in multiple views. External position measuring systems such as: 3D tracking devices, Global Position Systems, telemetry of manipulators or other positioning devices, translation and orientation sensors are often used. The observed features may already exist in the scene or on the object or may be placed there. The preferred case is when only existing features are used, however, in the prior art this is not as reliable and accurate as using artificial features (markers, beacons). Feature selection and matching of observed objects is often performed manually, which is labour intensive and inaccurate. Automatic feature selection and matching algorithms exist but are less accurate and reliable.

Creating 3D models of an environment often requires fusing data from different sensors. One sensor (especially with fixed optics and at one stand-off distance) cannot provide the resolution and depth of field required for the whole range of operations, e.g., room model and blood spatter analysis. Data from multi-modal sensors has to be fused together, e.g., room model and close-up images of fingerprints. At present, this problem is dealt with using manual data registration using existing features visible in images from multiple cameras, installation of unique targets that make the manual or automatic registration easier, and a GPS-like system that tracks position and orientation of cameras and sensors (Magnetic (e.g., Polhemous), LEDs (e.g., Optotrack), optical tracker (e.g., 3rdtech)).

In the case of underground mine mapping, particularly, after generating 3D mine models using stereo cameras, it is difficult to register the models accurately with the mine map. It would be highly desirable to have one device that can automate the process to capture geological, geotechnical, survey and other management information, and as a result, only one individual will need to collect data for use by everyone. In the existing art, 3D modelling systems (both laser-based and camera-based) are not able to register to the mine map accurately themselves and require additional equipment. On the other hand, total stations can locate themselves accurately but only provide very sparse 3D point data without photo-realism.

U.S. Pat. No. 6,009,359 issued to El-Hakim et al. discloses a mobile 3D imaging system which includes a movable platform; several image cameras mounted on the movable platform for capturing intensity images of the region being imaged. The system includes a range imaging device coupled to the movable platform in a known relationship to the cameras. A 3D model is obtained by correlating the intensity images and the range images using knowledge of the predetermined locations of the cameras and the range imaging device and generating a model in dependence upon the correlation. This system uses a scanning rangefinder to capture range information, and separate cameras to capture images and to determine location of the mobile platform. As the scanning rangefinder collects the range data sequentially the mobile platform must remain stationary during the acquisition. The scanning rangefinders are relatively larger, more expensive and more susceptible to shock and vibration as compared to stereo cameras proposed in this invention. Additionally, the stereo cameras can capture images within much shorter time (in order of microseconds or less) than scanning rangefinders (seconds to minutes) allowing for operation from a mobile platform without stopping for data acquisition. The proposed solution uses the same cameras to capture images used for localization and 3D computation. These factors reduce the size, weight and cost, and increase the robustness of a camera based 3D modeling systems as compared with systems that use scanning rangefinders.

U.S. Pat. No. 6,781,618 issued to Beardsley discloses a method for constructing a 3D model of a scene using two cameras having a physical relationship together. The first camera is used to acquire images of unknown scene, from which a model is created and the second camera acquires images of a special registration pattern or a rigid structure. The limitation of this method is that it requires placing the registration pattern in the modeled environment and that the pattern always be visible in the second camera images.

U.S. Pat. No. 6,711,293 issued to Lowe discloses a method and apparatus for identifying scale invariant features in an image and use of same for locating an object in an image. Lowe detects scale invariant features in training images of objects and stores them in a database. The objects are recognized in images by detecting features in new images by matching these features with features detected previously and stored in a database. The features are two dimensional only as Lowe uses a monocular camera, and he does not match the features temporally to recover the camera motion.

U.S. Pat. No. 4,991,095 issued to Swanson is directed to a method of mathematical modeling of underground geological volumes for mapping layers of sedimentary deposits which models geologic volumes having critical bounding surfaces and inclined, stacked layers of sedimentary deposits. The method involves composing a model volume analogous to the actual volume wherein the model volume includes layers of cells arranged in vertical columns of cells, which are inclined and stacked analogous to the layers of deposits in the actual volume.

Therefore, it would be very advantageous to provide a method for creating three-dimensional (3D) computer models which avoids the above mentioned drawbacks.

SUMMARY OF THE INVENTION

The present invention provides a method and apparatus for producing photorealistic 3D models of environments and/or objects from a plurality of stereo images obtained from a mobile stereo camera. The cameras may be handheld, mounted on a mobile platform, manipulator or a positioning device.

In one aspect of the invention there is provided a method of producing a three-dimensional (3D) model of an environment, comprising the steps of:

a) acquiring a first and second plurality of successive stereo images of an environment from one or more stereo cameras which are moving with respect to the environment, each of the one or more stereo cameras having at least two individual image capture means where there is an overlap between images captured by said at least two individual image capture means;

b) for each image of said first plurality of successive stereo images, detecting features in the stereo images and computing a 3D position and descriptor for each detected feature, and storing said 3D position and said descriptor as a 3D feature in a database;

c) for each image of said first plurality of successive stereo images, computing relative motion of the one or more stereo cameras with respect to the environment by matching the detected features in the stereo images with said 3D features stored in the database using descriptors of said 3D features;

d) for each image of said second plurality of successive stereo images, computing dense 3D data sets, representative of the environment from-one or more range sensing devices;

e) for each image of said second plurality of successive stereo images, transforming the computed dense 3D data from step d) into a selected coordinate frame of reference using the computed relative motion from step c) to give transformed dense 3D data in the selected coordinate frame of reference; and f) storing the transformed dense 3D data for each image of said second plurality of successive stereo images and producing a 3D model of the environment from the stored transformed dense 3D data. Another embodiment of the present invention provides an apparatus for producing a three-dimensional (3D) model of an environment, comprising the steps of:

a) one or more stereo cameras for acquiring a first and second plurality of successive stereo images of an environment from said one or more stereo cameras which are moving with respect to the environment, each of the one or more stereo cameras having at least two individual image capture means where there is an overlap between images captured by said at least two individual image capture means;

b) processing means programmed with instructions for i) detecting, for each image of said first plurality of successive stereo images, features in the stereo images and computing a 3D position and descriptor for each detected feature, and storing said 3D position and said descriptor as a 3D feature in a database;

ii) each image of said first plurality of successive stereo images, computing relative motion of the one or more stereo cameras with respect to the environment by matching the detected features in the stereo images with said 3D features stored in the database using descriptors of said 3D features;

iii) each image of said second plurality of successive stereo images, computing dense 3D data sets, representative of the environment from-one or more range sensing devices;

iv) each image of said second plurality of successive stereo images, transforming the computed dense 3D data from step d iii) into a selected coordinate frame of reference using the computed relative motion from step ii) to give transformed dense 3D data in the selected coordinate frame of reference; and v) storing the transformed dense 3D data for each image of said second plurality of successive stereo images and producing a 3D model of the environment from the stored transformed dense 3D data.

Another embodiment of the present invention provides a method of producing a three-dimensional (3D) model of an underground environment, comprising the steps of:

a) acquiring 3D information of an underground environment from at least one range sensing device;

b) producing a 3D surface model of the underground environment from the acquired 3D information suitable for visualization, analysis or post-processing;

c) acquiring an image of said underground environment from a camera;

d) texturing the 3D surface model with said image;

e) locating the range sensing device by back-sighting to at least two existing survey stations located in the underground environment using a second range sensing device in a fixed relationship to said first range sensing device; and f) based on the position information from step e, transforming the 3D model of the underground mine to a map of the underground environment in a coordinate frame of reference of the underground environment.

The present invention also provides an apparatus for producing a three-dimensional (3D) model of an underground environment, comprising the steps of:

a) at least a first range sensing device for acquiring 3D information of an underground environment; and b) processing means programmed with instructions for i) producing a 3D surface model of the underground environment from the acquired 3D information suitable for visualization, analysis or post-processing;

ii) acquiring an image of said underground environment from a camera;

iii) texturing the 3D surface model with said image;

iv) locating the range sensing device by back-sighting to at least two existing survey stations located in the underground environment using a second range sensing device in a fixed relationship to said first range sensing device; and v) based on the position information from step iv), transforming the 3D model of the underground mine to a map of the underground environment in a coordinate frame of reference of the underground environment.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which.

DETAILED DESCRIPTION OF THE INVENTION

As used herein, the phrase "monocular camera" means an image recording device that projects an image of the observed scene through an optional lens onto a photosensitive element (e.g., CCD, CMOS) and equipped with means for transferring thus image to an image processing device (e.g., a computer).

As used herein, the phrase "stereo camera" means a device that comprises two or more monocular cameras described above and observing approximately the same scene from a somewhat different point of view (the cameras may be combined in one enclosure).

As used herein, the phrase "auto-referencing" means an automatic method (algorithm) to establish correspondence (reference) between two or more data sets by detecting and matching common elements in the data sets.

As used herein, the phrase "tie-points" means distinctive local features that are matched between the stereo images taken at the same time or between stereo images taken at different time. Tie-points typically refer to salient features at regions with large contrast of intensity such as corners, edges or interest points in 2D images or in 3D which are repeatable and are likely to be recognized. Each tie point usually includes some sort of appearance descriptor that can facilitate subsequent matching. The term "descriptor" refers to one or more distinctive labels or identifiers represented typically as a vector of numbers which can be matched between tie-points.

As used herein, the phrase "point cloud" means a data set of three-dimensional points. Point clouds may be produced by 3D digitizers and describe the surfaces of digitized objects.

As used herein, the phrase "dense 3D data set" means a point cloud where a large proportion of all possible measurements obtained from a digitizer are represented in the data set.

As used herein, the phrase "surface mesh" means a digital representation of a surface as a collection of polygons in 3D space.

As used herein, the phrase "Ego Motion estimation" means an ability to estimate motion of a camera relative to observed scene or objects using image sequences obtained from this camera. This also includes the case when the object is moving and camera is stationary.

As used herein, the phrase "Underground environments" includes underground spaces such as passages, mines, tunnels, voids, caves and sub-terrain cavities.

As used herein, the phrase "Rangefinder" means a range measuring device used to accurately measure the range to a target. The range measurement can be based on various principles such as time-of-flight, triangulation, phase difference, etc.

As used herein, the term "total station" means a land survey instrument that combines the angle-measuring capabilities of a transit with electronic distance measurement.

3D Imaging System

Figure 1:
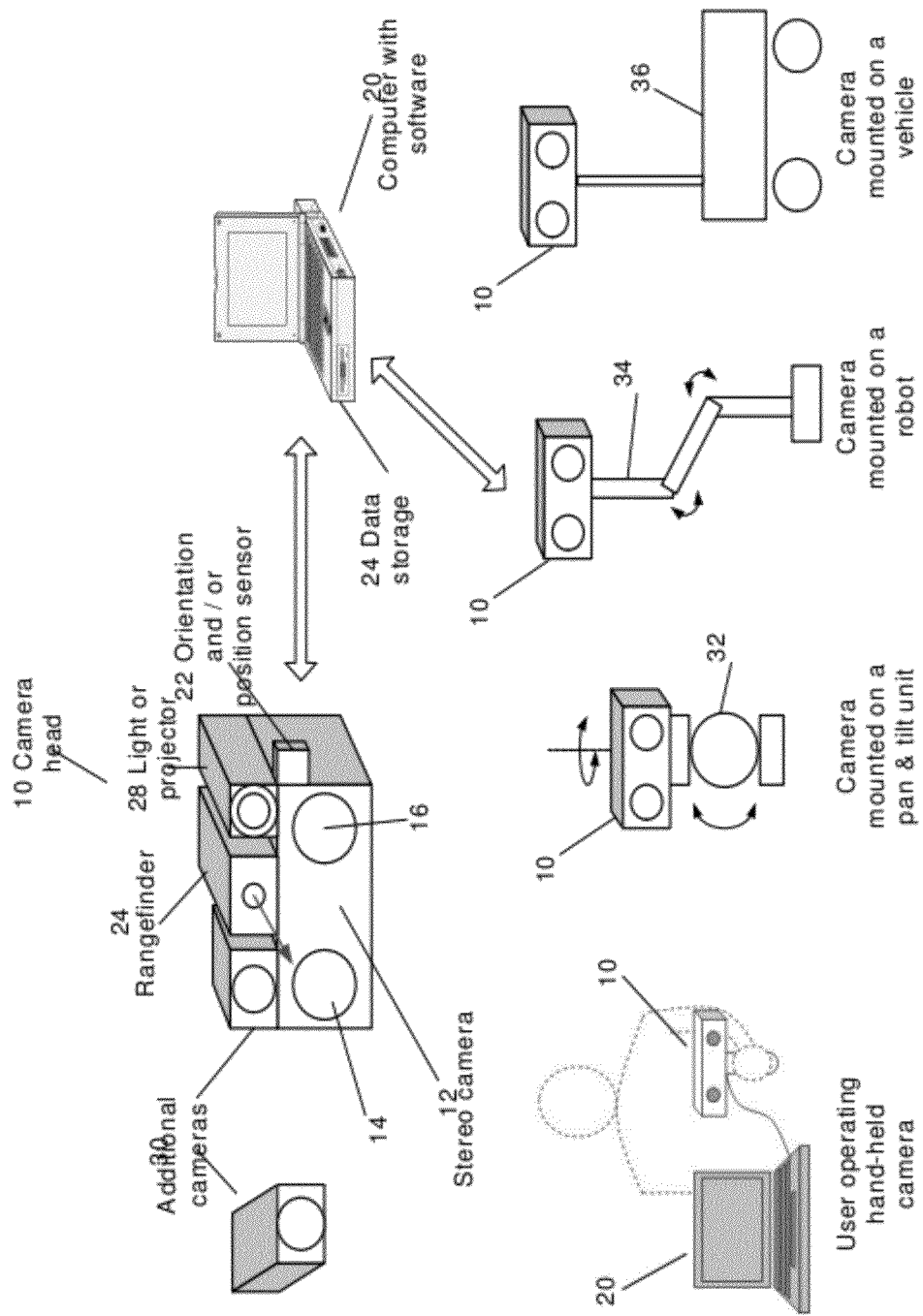
FIG. 1 is an illustration of a 3D imaging system illustrating its different configurations according to the present invention.

The present invention provides a method of producing a three-dimensional (3D) model of an environment, using a 3D imaging system. Referring to FIG. 1, a 3D imaging system constructed in accordance with the present invention is shown generally at 10 and includes one or more stereo cameras 12 each comprised of two or more separate cameras each, with FIG. 1 showing the stereo camera 12 having two individual cameras 14 and 16. The stereo camera(s) 12 may be hand-held, or mounted on a tripod, camera positioning device such as Pan and Tilt Unit (PTU) or a robotic manipulator, or a vehicle. The relative locations of the monocular cameras 14 and 16 (making up the stereo camera 12) with one another remain constant, with intersecting fields of view. A computer processor 20 with software includes a data storage device. The imaging system 10 may also include orientation, position, velocity and acceleration sensors 22, as well as one or more ranging or rangefinder devices 24. The imaging system 10 may include optional additional cameras 30, lights and a pattern projector 28.

Figure 2:
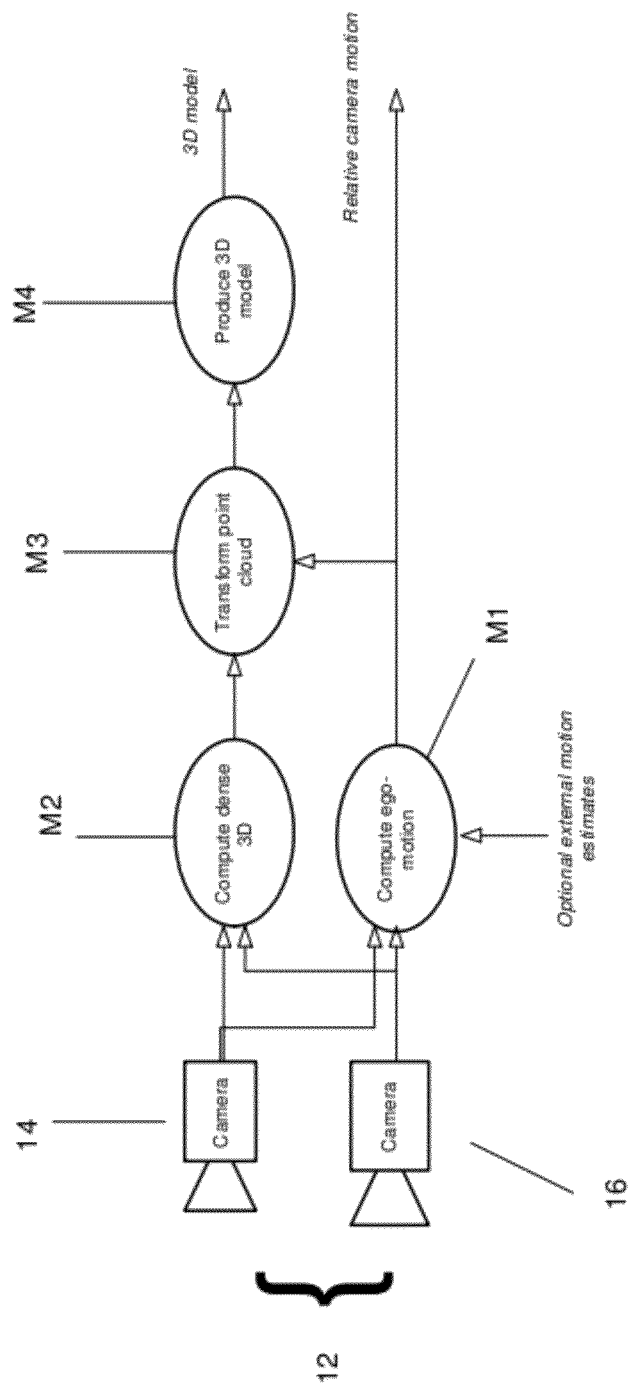
FIG. 2 is a block diagram showing the principle of operation of the 3D imaging system of FIG. 1.
Figure 3:
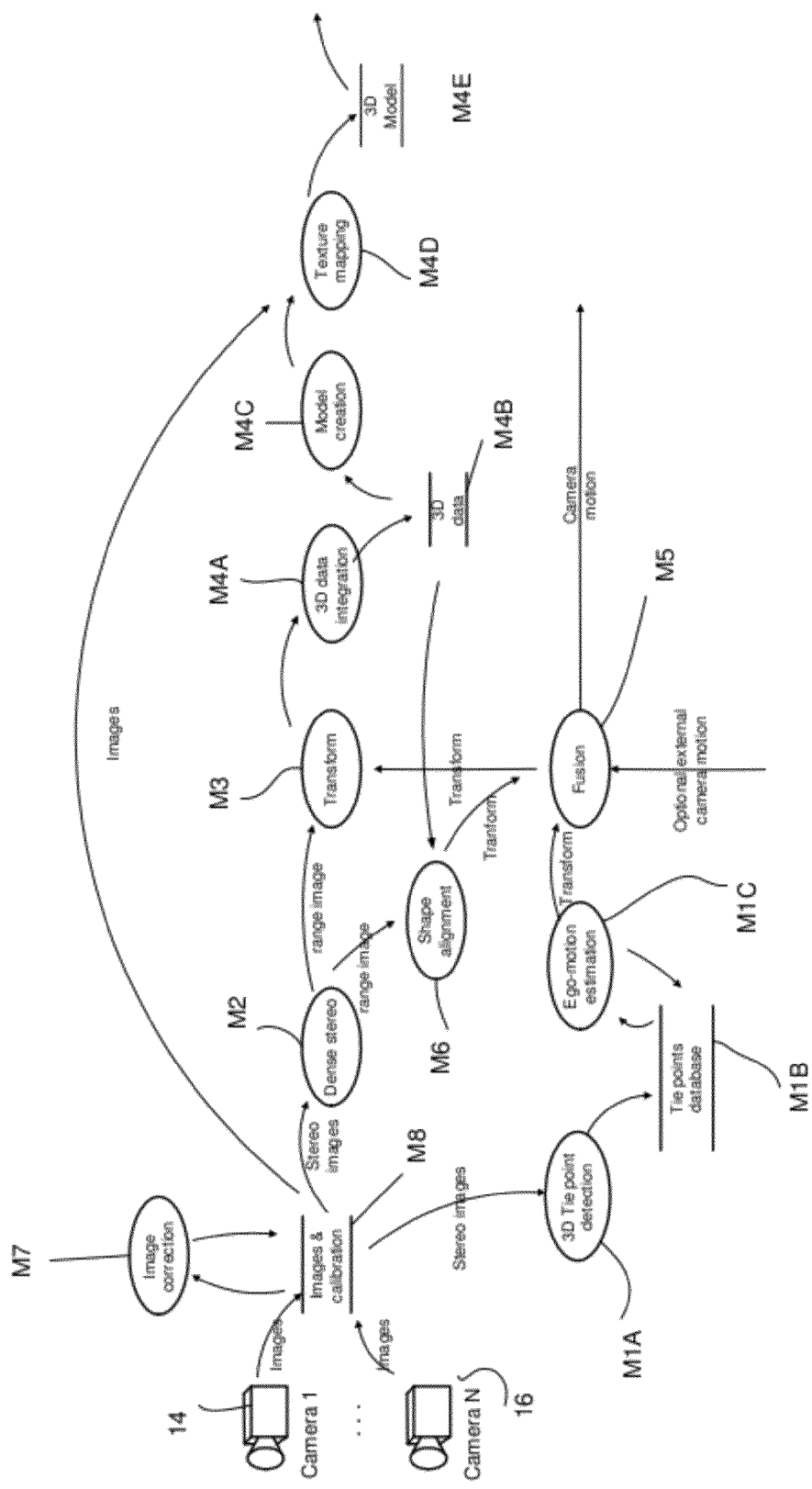
FIG. 3 is a block diagram showing details of the data processing in the 3D imaging system expanding the information provided in FIG. 2.

Referring to FIGS. 2 and 3, when only one stereo camera 12 is used, the method involves acquiring a plurality of images from one stereo camera 12 wherein there is an overlap between the stereo images acquired by the two individual cameras 14 and 16 making up camera 12, acquiring a plurality of images from stereo camera 12, then detecting features in pairs of stereo images (the pair being made up of one image each from the monocular cameras 14 and 16), computing the 3D positions and descriptors for the detected features, and storing these positions and descriptors in a database. The camera motion is computed by matching 3D features detected in new stereo images and those detected previously and stored in the database. Moreover, features may be detected in dense 3D data from successive frames and matched with features previously detected and stored in the database. Alternatively, the dense 3D data sets can be aligned to obtain camera motion but preferably, the camera motion obtained by aligning the 3D data is combined with the feature based camera motion estimation.

When two or more stereo cameras 12 are used they are placed in fixed spatial relationship to each other, e.g., combined into one unit but having different fields of view, and the method involves calibrating the relative position and orientation of the cameras and of computing the camera motion by combining 3D features computed from all of the cameras first using the intra-camera calibration.

When two or more stereo cameras 12 are used and their relative positions to each other are unknown then the cameras are first used independently to capture image sequences and the resulting 3D models created using each camera images are auto-referenced. The method includes auto-referencing of multiple sequences by matching 3D features detected separately for each sequence and stored in separate databases. The auto-referencing method is described in more detail below. The multiple sequences may be obtained from one camera used in the same environment or from different stereo cameras.

FIG. 2 shows a block diagram that illustrates the principle of the system operation. Stereo images are sent to two modules, module 1 (M1) and module 2 (M2). Module 1 (M1), entitled "Compute ego-motion" processes stereo image sequences from cameras 14 and 16 and computes the motion of the stereo camera 12. The module M1 may use additional information from external sensors comprising one or any combination of the following or equivalent sensors: inertial measurement devices (e.g., gyroscopes, inclinometers, compasses, accelerometers), Global Positioning Systems (GPS), wheel odometry or pedometers, telemetry from a manipulator or a camera positioning device, or camera pose tracking devices. By combining information from optional sensors with the camera ego-motion estimation it is possible to increase the motion estimation accuracy and reduce the amount of necessary processing.

Module 2 (M2), entitled "Compute dense 3D" computes 3D representations for the stereo images acquired by each camera 14 and 16. M2 is the dense stereo routine which computes dense 3D data from pairs of stereo images (the pair being made up of one image each from the monocular cameras 14 and 16) by matching image intensity or color distributions between the stereo images. Any of the known dense stereo algorithms, such as Correlation, Sum of Squared Distances (SSD), or graph-cut based algorithms can be used. A pattern projector 28 may optionally be used to project a random dot pattern onto the environment or object, to improve the coverage of dense 3D data computed by M2.

In the preferred embodiment described here modules M2 and M1 process images from the same stereo camera 12. The same images may be processed by both modules or one of the modules may process only a subset of images. Typically, motion estimation M1 requires more images to obtain good motion estimate than M2 to obtain good coverage of dense 3D data. This is convenient and cost effective as only one set of cameras is required. However, the M1 and M2 may use two different stereo cameras 12 with different fields of view, as long as the spatial relationship between these cameras is known and temporal relationship between images acquired by both sets of cameras is known. The spatial relationship (relative position and orientation) between the cameras may be known from the design drawing and/or may be obtained through a camera calibration process. Knowledge of the temporal relationship between the images from both cameras is necessary to apply the computed motion by Module M1 to the computed dense 3D data by Module M2 correctly. This may be achieved by synchronizing image acquisition for both cameras or by storing time stamps for all images and by using interpolation to obtain relative camera location.

In another embodiment of the invention, module M2 may use information, not from a stereo camera 12 per se, but from any range sensing devices such as a scanning or non-scanning rangefinder. In this embodiment the spatial relationship between the range sensing device and the stereo camera needs to be known, and the temporal relationship between the acquired range data and stereo images must be known.

Module 3 (M3), entitled "Transform Point cloud" receives data from both modules M1 and M2 and transforms all 3D points computed in Module 2 into one selected coordinate frame using the relative camera motion estimated by Module 1. This data is integrated and used in Module 4 (M4), entitled "Create Surface and Map Texture" to create a 3D model, which may be represented as a point cloud, surface mesh or a 3D shape. Point clouds are typically used to represent raw measurements as 3D points. The points may be assigned different colors (intensities) representing their optical or other properties.

Surface meshes are typically created from point clouds and used to represent observed surfaces of objects. The surface meshes may be augmented with color and textures obtained from cameras or other sensors. Collections of 3D points may be represented analytically as 3D geometrical shapes (cubes, spheres, cylinders etc.). Their surfaces may be augmented with color and textures representing properties of the observed objects. Selection of a representation depends on the type of the observed objects/scenes, processing requirements/limitations and display devices. Man-made objects can be efficiently represented as 3D shapes whereas natural surfaces are more efficiently represented as surface meshes or point clouds.

FIG. 3 shows the details of the processing and corresponding software modules outlined previously in FIG. 2. Previously introduced Module M1, Compute Egomotion, consists of Module M1A, entitled "Tie Point Detection", Module M1B, entitled "Database of Tie Points" and Module M1C, entitled "Ego-motion Computation". Module M1A detects 3D tie points in the stereo images. The tie-points are distinctive local features that can be detected in images. Module M1A may include a corner detection algorithm or Scale Invariant Feature Transform (SIFT) to detect 2D tie-points in individual images. Module M1A first detects the tie points in each image independently, matches them between two or more stereo images using similarities in 2D tie-point appearances or descriptors and computes their 3D locations providing 3D tie-points. Alternatively, the 3D tie-points may be detected directly in dense 3D data computed from stereo images, such as produced module M2 introduced in FIG. 2.

Module M1C entitled "Ego Motion estimation" is a module which estimates camera ego-motion by matching, validating and computing a transformation between the 3D tie points produced by Module M1A and those stored in the database M1B. If new tie-points are detected then they are added to the database M1B. This module will be described more fully below.

Module M2 was previously introduced in FIG. 2 and entitled "Compute dense 3D".

Module M6, entitled "Shape alignment" is an alternative shape alignment routine which may be used to align the dense 3D data obtained from successive stereo pairs or by aligning current 3D data sets with previously integrated 3D data and stored in a 3D point database Module M4B. This may be particularly useful when not enough tie-points can be detected or they are not well distributed in the images (e.g., occupy only a small portion of the camera field of view). Such situations are more likely to occur when modeling objects as opposed to modeling environments. The shape alignment module operates by matching partial 3D reconstructions and it may use an algorithm such as Iterative Closest Point (ICP). ICP minimizes distances between two 3D shapes represented as point clouds or surface meshes. Different ICP versions exist and differ in their performance, metric used as a distance measure and how they deal with outliers. In some cases it is beneficial to use both camera ego-motion estimation (Module M1) and shape alignment (Module M6) for the same data sets. Modules M1 and M6 may be used then in sequence, iteratively or simultaneously.

Module M5, entitled "Fusion" is a module which combines camera motion estimates produced by Module M1C, "Ego-motion estimation", (essentially the output of Module M1 in FIG. 2 "Compute egomotion",) Module M6, "Shape alignment", with the measurements from any optional external sensors if they are available and if it is useful to do so. The external sensors may comprise one or any combination of the following or equivalent sensors: inertial measurement devices (e.g., gyroscopes, inclinometers, compasses, accelerometers), Global Positioning Systems (GPS), wheel odometry or pedometers, telemetry from a manipulator or a camera positioning device, or camera pose tracking devices. By combining information from optional sensors with the camera ego-motion estimation it is possible to increase the motion estimation accuracy and reduce the amount of necessary processing.

Module M3, discussed previously as module M3 in FIG. 2 and entitled "Transform point cloud", is a transform module which transforms dense 3D data into a selected coordinate frame. A coordinate frame associated with any camera location during acquisition of the image sequence can be used. Typically, the coordinate frame of the first image is used so that all the 3D data is acquired relative to the starting location of the camera sequence but this is not essential.

Module M4A, entitled "3D data integration" is a routine which integrates the transformed dense 3D data from Module M3, eliminates redundant measurements, and reduces effects of noise and outliers. The 3D points are accumulated in a Module M4B, which is a 3D database.

Module M4C, entitled "Model creation" is a routine which creates, from 3D data stored in the 3D database M4B, a 3D representation suitable for display or further processing, for example a 3D mesh or surface or a point cloud.

Module M4D, entitled "Texture mapping" is a routine which selects texture images (color, infrared or intensities obtained at other wavelengths) or data obtained from other sensors and applies these textures to the 3D representation produced by Module M4C.

Module M7 is an optional image correction module which corrects image intensity (e.g., for Vignetting effects and multi-exposure fusion) and corrects image geometry, for example it corrects for lens distortions and performs image rectification. When Module M7 is used, the stereo images are obtained directly from the stereo cameras 14 and 16 and after the images have been corrected, they are returned to Modules M1A and M2 as discussed above.

The images obtained from the cameras may be stored in the image database M8 together with the camera calibration information.

Multiple 3D representations created from different sequences can be registered and merged together by auto-referencing, with details described below.

A significant advantage of the 3D imaging system disclosed herein, as compared with previous systems, lies in the use of natural tie points for camera ego-motion estimation and subsequent use of this ego-motion for registration of the 3D data obtained by processing the camera images. This data registration may be combined with other methods for camera motion estimation (shape alignment and/or access to external motion data), which increase the registration accuracy and robustness and speeds up the processing. The proposed invention creates photo-realistic 3D models from a mobile stereo camera automatically, which allows visualization and measurements.

Method of Auto-Referencing Stereo Camera

The present invention also provides a method that can auto-reference (globally localize), stereo camera 12 without any prior camera pose information. This method can also be applied to compute relative alignment between multiple feature databases to obtain the camera position in one scan with respect to another scan. This allows creating and combining models from multiple stereo sequences obtained with one or more stereo cameras.

Figure 4:
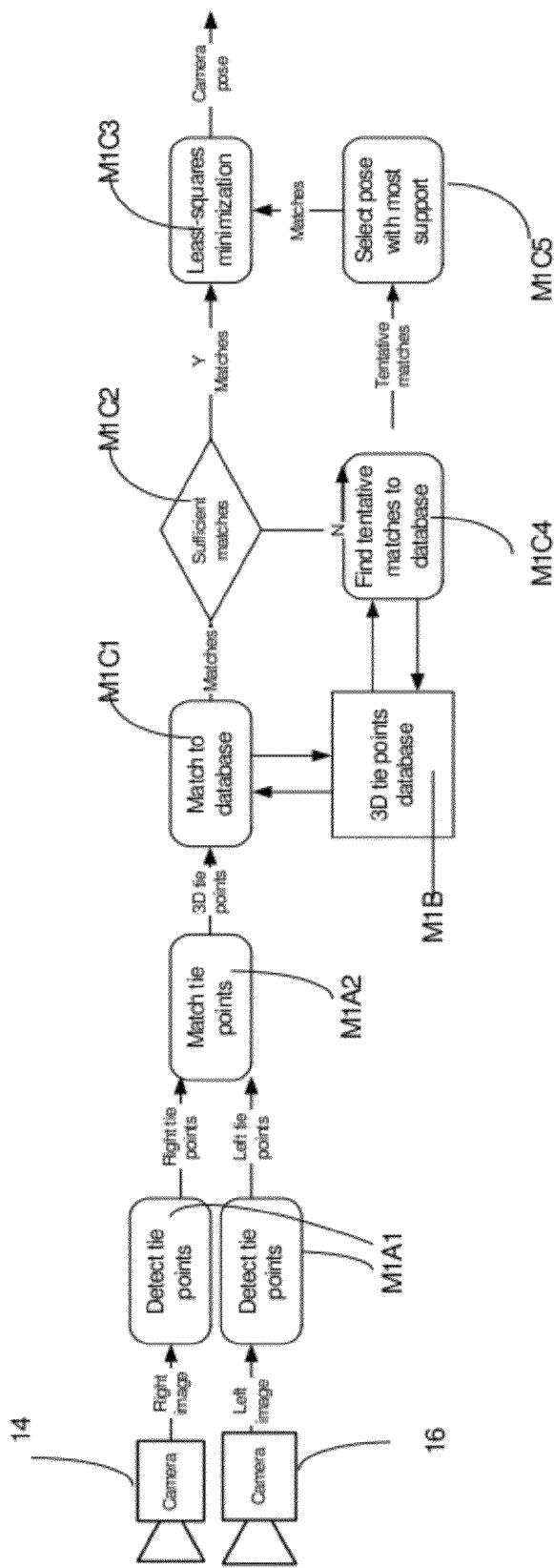
FIG. 4 shows a block diagram of a method for data processing of the self-referencing stereo camera.

Referring to FIG. 4, the method of self-referencing includes the following steps. When the camera 12 is moved around, a sequence of stereo images is captured by the stereo camera 12, with overlap between frames captured by the individual cameras 14 and 16.

Module M1A "3D Tie point detection" in FIG. 3 is broken down into sub-modules M1A1 and M1A2 in FIG. 4. Tie points, for example Scale Invariant Feature Transform (SIFT), are detected in each of the stereo images (M1A1). Each feature has an associated SIFT descriptor vector that characterizes the feature which is stored in a database. The tie points are then matched across the right and left images to obtain 3D tie points, based on the SIFT descriptor vector and epipolar constraint (M1A2). The SIFT descriptor vector provides a highly specific description of the feature to facilitate matching. The epipolar constraint, known from geometry of stereo cameras, reduces the search for matches from two to one dimension, as the corresponding match of each feature lies on a line as specified by this constraint.

Module M1C "Ego-motion Estimation" in FIG. 3 is broken down into sub-modules M1C1, M1C2, M1C3, M1C4, M1C5 in FIG. 4. The camera motion is computed by matching 3D tie points from newly acquired stereo images with those stored in the database (M1C1), based on the SIFT descriptor vector if the camera location is approximately known from earlier images (tracked), then tie points locations may be predicted, which is faster than searching the whole database. Alternatively, the matching may be performed by searching the whole database, which is slower, does not require any knowledge of the camera location and may be used when the tracking was lost. When the camera moves around in an environment, tie points are detected. Some of the tie points have been observed previously and can be matched to the database while new tie points not observed previously are added to the database.

If there are sufficient matches, the tracking mode is successful (M1C2). Least-squares minimization is carried out to estimate the camera motion that will minimize the predicted feature location with the measured feature location in the image (M1C3). Matches with large errors are discarded as outlier and the least-squares minimization is repeated to obtain a 6-degree of freedom camera pose.

If there are not sufficient matches, e.g., when the tracking is lost, global localization described as follows is carried out. First, tentative matches are found between the current tie points and the entire database, based on the SIFT descriptor vector (M1C4). Then, three tentative matches are randomly selected to compute a pose hypothesis, and the number of supporting matches is found for each pose hypothesis (M1C5). This process is repeated multiple times and the pose hypothesis with most support is selected, and all the supporting matches for this hypothesis are used in a least-squares minimization to obtain a 6 degree of freedom camera pose. When the user starts a new scan, the global localization procedure can be used first to locate the new camera location relative to a previous scan, and then the tracking mode can continue.

After estimating the camera ego-motion, the next image pair is considered and the process repeats until the end of image sequence.

When two sequences of stereo images have been captured, the relative alignment between the two databases of tie points (SIFT features) can be computed, i.e., to obtain camera position of one scan with respect to another scan, we refer this procedure as auto-referencing.

Figure 5:
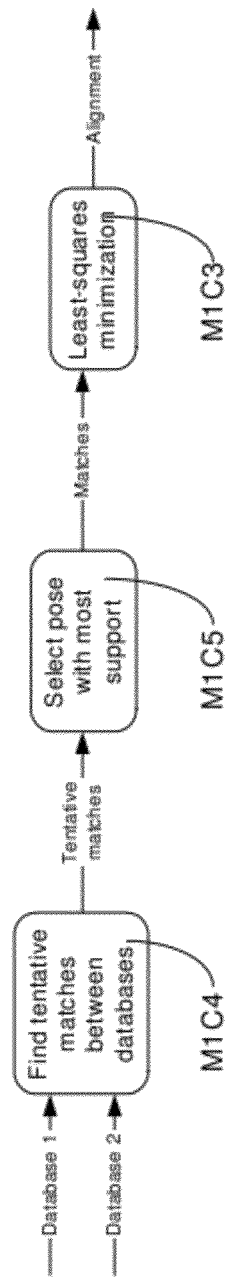
FIG. 5 shows a block diagram showing a method for aligning two scans of the self-referencing stereo camera.

Referring to FIG. 5, the procedure to find the relative alignment between the two sequences of captured stereo images with overlap and stored in two databases is as follows. The method includes finding the tentative matches between the tie points in the two databases (M1C4). Then, three tentative matches are randomly selected to compute a pose hypothesis, and the number of supporting matches is found for each pose hypothesis. This process is repeated multiple times and the pose hypothesis with most support is selected (M1C5). All the supporting matches for this hypothesis are used in a least-squares minimization carried out in which features with least-squares errors larger than a preset threshold are discarded as outliers, and the least-squares minimization is repeated to obtain a 6 degree of freedom camera pose (M1C3). The minimization is based on the expected projection of the database features and the actual feature location on image. This can be extended to aligning multiple sequences in a pair-wise fashion.

Unlike many prior art 3D imaging systems, the present method for self-referencing stereo camera 12 advantageously does not require a tracking device or inertial sensors to self-reference itself so that the camera can operate in an unknown environment. When mounted on a mobile platform such as a vehicle, it can recover vehicle motion, i.e., visual odometry.

A significant advantage of this method of self-referencing stereo camera 12, as compared with the state-of-the-art, lies in the use of natural tie points for camera ego-motion estimation, the global localization capability to resume tracking when tracking is temporarily lost and also the auto-referencing capability of registering multiple stereo sequences together automatically.

Method and an Apparatus for Registering Data from Multiple Cameras and Sensors

In some applications, for example, crime scene investigations, it is useful to combine images captured with additional cameras (e.g., close-up, high resolution, and operating beyond the visible spectrum) of objects of interest or measurements from other sensors (e.g., biological and chemical) with 3D models. In mining, it is often necessary to measure mineral concentrations on the mine face using contact sensors or to take samples for assay analysis. In general, it is difficult to record the accurate locations where the objects in images were relative to the scene due the large number of images, small field of view or dissimilar appearance caused by the use of different wavelengths (multi-spectral imaging). Also, the camera or other sensor location during image/data acquisition is normally not recorded unless a special 3D tracking device is used.

Any combinations of the configurations of the 3D Imaging System shown in FIG. 1 and the data processing methods disclosed in FIGS. 2 to 5 can be used to create the 3D model.

Figure 6:
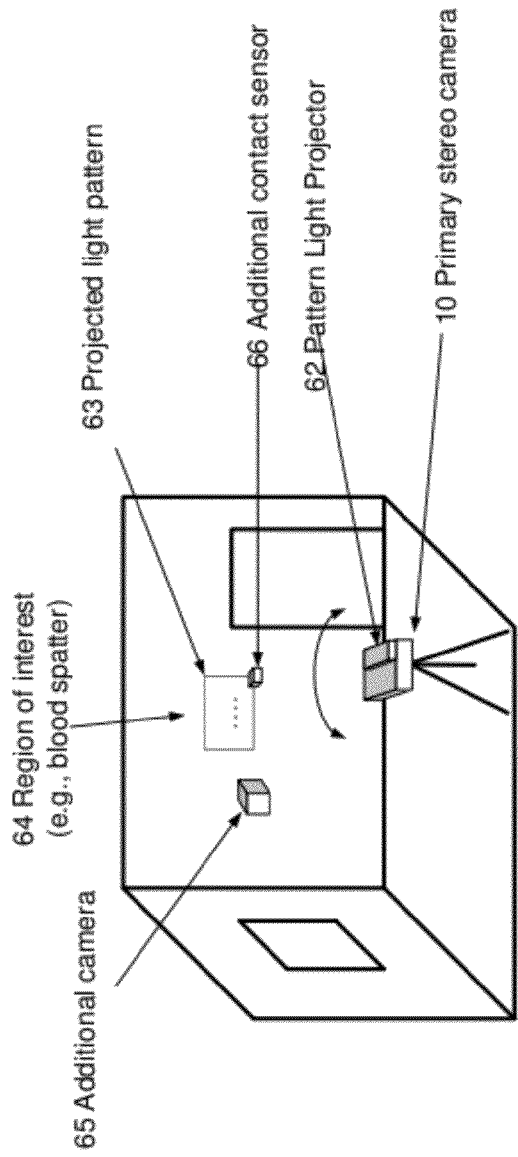
FIG. 6 shows an apparatus for enhancing 3D models by registration of data from additional sensors or cameras using a stereo camera with the pattern projector and an additional (e.g., close-up) camera or a contact sensor.
Figure 6:
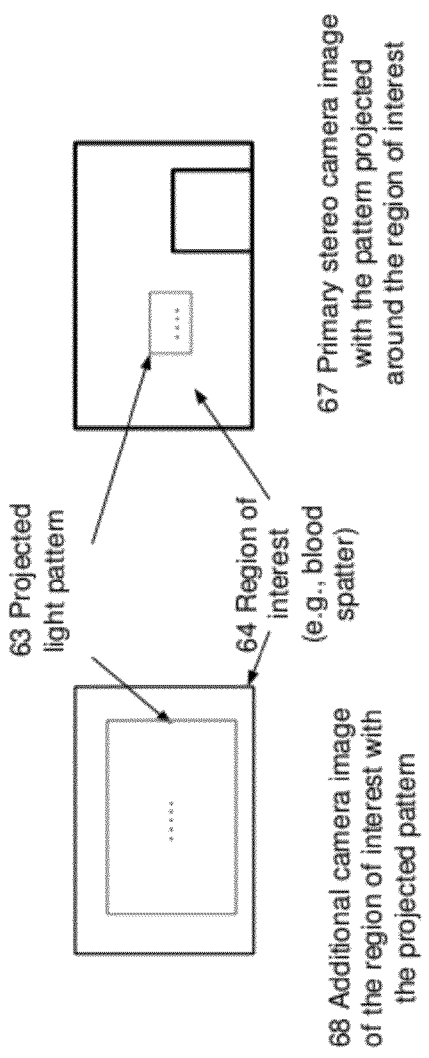

A system shown in FIG. 6 consists of a primary stereo camera 12, which is integrated and calibrated with a light pattern generator 62. Both units are coupled together and may be mounted on a pan and tilt unit on a stationary tripod, mobile platform or be hand-held. The light pattern 63 can be interactively directed by commanding the PTU and/or moving the head 10 towards a region of interest 64 (e.g., fingerprint, blood spatter, mineral). 3D location of the projected pattern may be then recovered by reconstructing a 3D model of the scene, using techniques described earlier with respect to the method and apparatus of FIGS. 2, 3, 4 and 5 and finding intersection of the projected light with the model surface as location of the primary camera/light pattern source is known in the 3D model. Images of the region of interest 64, captured with the additional camera 65, will contain the projected pattern so that the images can be registered with the 3D model.

The projected pattern may 62 consist of a shape (e.g., a rectangle) outlining the region of interest and may include features (e.g., asymmetrical elements) that allow and simplify correct matching of images 67 from the primary camera 12 with images 68 from the additional camera 65. The patterns may contain embedded identification features, for example, barcodes, two dimensional codes or numbers that will help in establishing correspondence between the additional and primary camera images of the selected regions of interest 64.

A contact or sampling sensor 66 may also be used to take measurements at regions of interest designated with the projector. The sensor 66 may be a chemical, biological or nuclear radiation probe such as used in forensic investigations. Alternatively, he sensor 66 may be a sensor such as X-ray fluorescence (XRF) or Laser Induced Breakdown Spectroscopy (LIBS) used for detecting presence of minerals or measuring mineral concentration in ore.

By matching images of regions of interest 64 in images 67 from the primary camera 12 and the images 68 from additional camera 65 it is possible to register such data with the 3D model and enhance the 3D model with additional data (e.g., higher resolution or multi-spectral). Similarly, measurements from the contact sensor 66 may be registered with the images 67 from the primary camera 10 and used to enhance the 3D model.

If the stereo camera 12 is hand-held or operated from a mobile platform then the cameras 12 and 65 should be synchronized or the images should be time-stamped allowing for accurate registration of images between both cameras.

The Light pattern generator 62 may have different embodiments, for example, it may use special optics and lasers (or other collimated beam sources) to project static patterns consisting of dots, lines, crosses, or any other arbitrary patterns. Alternatively, the patterns may be generated dynamically by a fast scanning device and a laser. If the complete pattern generation time is shorter than the camera exposure time, then it will be detected as a static pattern in the camera image. The dynamically generated patterns may be similar to the static patterns and may also include geometrical shapes and figures.

The additional camera 65 may be a monocular or a stereo camera, it may capture images at high resolution or be designed for close-up operations. It may capture images outside the visible spectrum (e.g., Infra-Red or Ultra-Violet), which are useful in forensic investigations. Other sensors such as radiation detectors may be used. It is necessary to assure that the projected light can be detected by the used camera or sensor (intensity and wavelength). If it is not then a camera that detects the projected pattern might be rigidly coupled and calibrated with the additional camera.

The sensor 66 may also be a sampling device used in forensic investigations or a device useful for measuring mineral concentration in ore in mining.

The images and point measurements may be hot-linked to the created 3D model allowing easy access. The images may also be re-projected as textures onto the 3D model surface providing locally high resolution/multi-modal details. Geometrically correct mapping will be obtained by identifying projected features in the additional camera images (e.g., points, lines, corners) and using them to correctly map these images onto 3D surfaces. An assumption on a local surface planarity will allow using an image homography to perform the mapping.

The method for registering data from multiple cameras and sensors is very advantageous in that it uses a light pattern projected from a projector connected to the primary stereo camera to enable registration of images from the additional camera with the 3D model created with the primary camera 12. This increases the fidelity of the created 3D models and allows combining of multi-modal measurements from different sensors.

Figure 7:
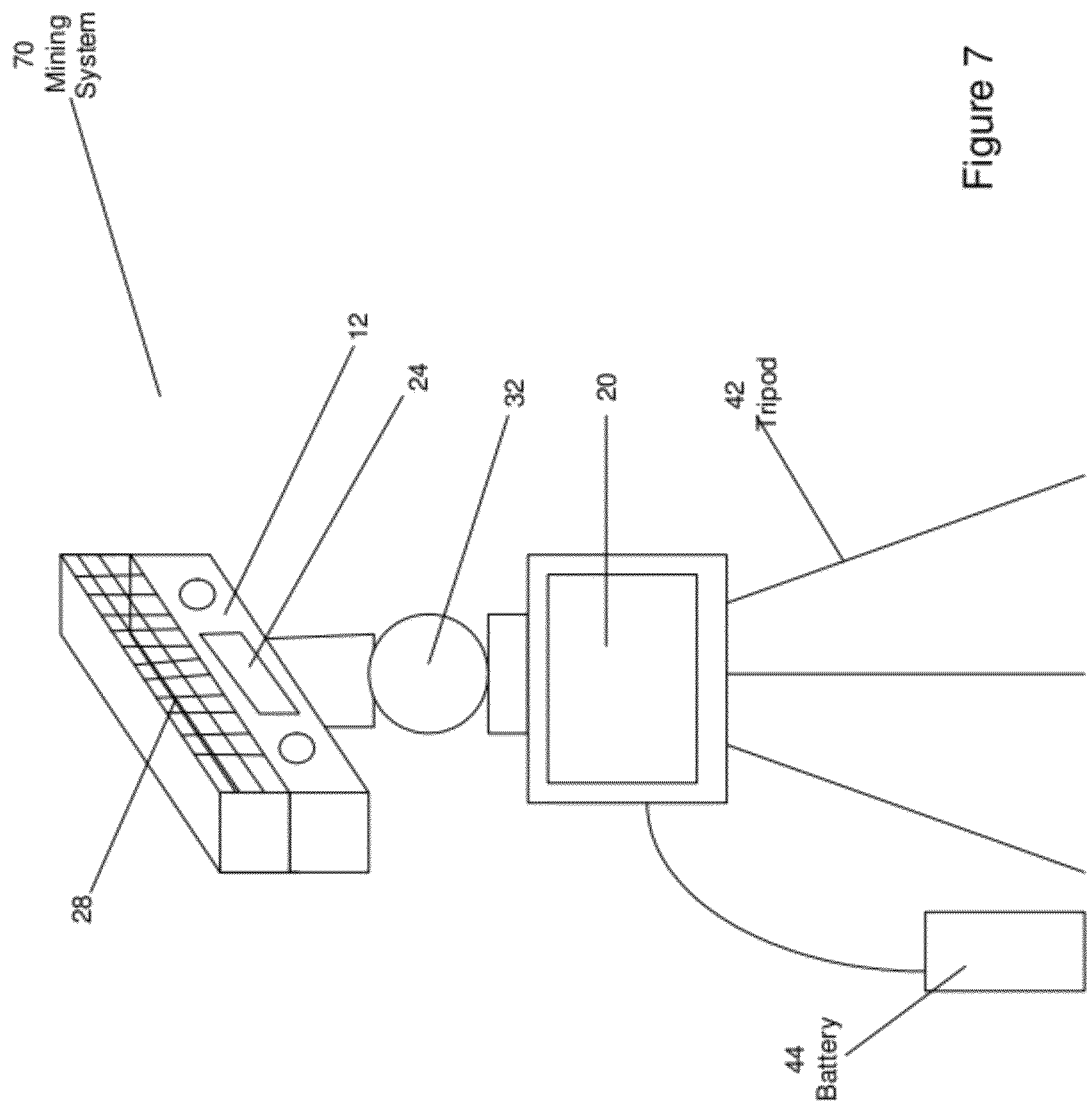
FIG. 7 shows a 3D imaging system for underground mining environments.

Automatic Reconstruction and Registration of 3D Mine and Cavity Models Using Stereo Cameras Integrated with Total Station The present invention also provides a method and apparatus for generating photo-realistic 3D models of mines (which also includes underground passages and caverns or other sub-terrain cavities) and automatically registering the models with a previously provided mine map. Referring to FIG. 7, the apparatus 70 includes a stereo camera 12 which includes two or more individual cameras 14 and 16 separated by a known distance, which may be the same as the stereo camera described in FIG. 1. The stereo camera 12 may be integrated with rangefinder 24 into a single unit. The stereo camera 12 and rangefinder 24 can be tilted and panned by a motorized pan-tilt unit (PTU) 32 mounted on a tripod 42. The rangefinder 24 together with the motorized pan-tilt unit 32 serve as a total station, i.e., to back-sight survey stations 86 (FIG. 8) to locate the system 70 in the mine coordinates.

Lights 28 may be mounted on the camera 12. A computer 20 is mounted on tripod 42. Batteries 44 provide power to the computer 20, camera 12, PTU 32, rangefinder 24 and the lights 28. Alternatively, the system components can be powered by external power.

It will be understood that camera 12 and rangefinder 24 do not need to be integrated into a single unit but may be physically separate, as long as their relative positions with respect to each other are known.

In its broadest, the method of producing a three-dimensional (3D) model of an underground mine includes acquiring 3D information (module M13 in FIG. 9) of an underground environment from at least one range sensing device and producing a 3D model (module M9 in FIG. 9) of the underground environment from the acquired 3D information suitable for visualization, analysis or post-processing. The method includes locating the range sensing device by back-sighting to at least two existing survey stations located in the underground environment and transforming the 3D model of the underground environment to a map of the underground environment.

Figure 8:
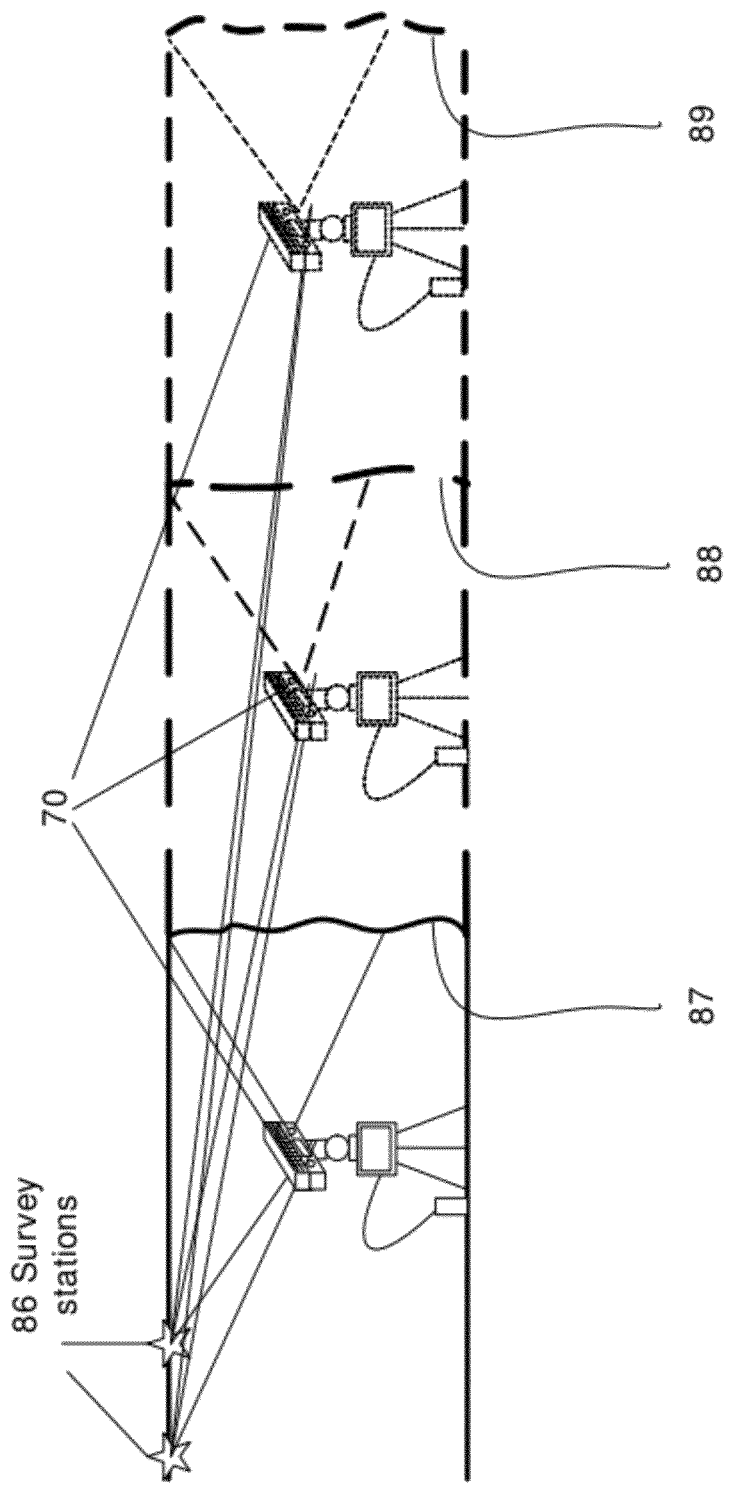
FIG. 8 illustrates how the 3D image system of FIG. 7 back-sights to existing survey stations for an advancing mine face.
Figure 9:
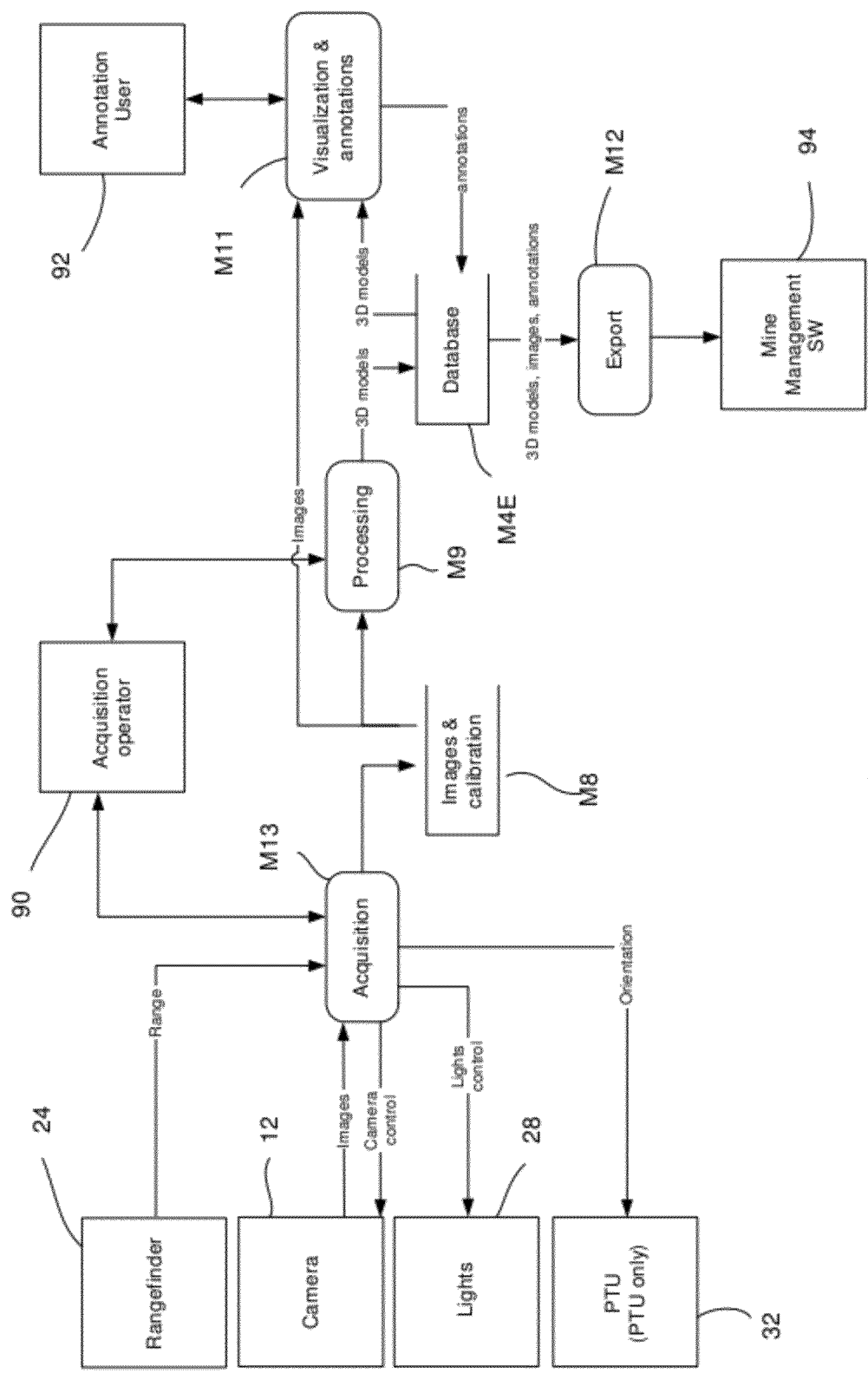
FIG. 9 shows a block diagram of data processing in the 3D imaging system for mining applications.

More particularly, referring to FIGS. 7, 8 and 9, the stereo camera 12 mounted on the pan-tilt unit (PTU) 32 captures a sequence of stereo images of the observed mine face 87 at different pan-tilt positions specified by the acquisition operator 90, the system then computes the 3D depth data from the stereo images and calibration data stored in M8, by matching the left and right stereo images captured by cameras 14 and 16, using module M2 as described above with reference to FIGS. 2 and 3. The dense 3D data is then transformed using the PTU/total station telemetry using module M3.

The dense 3D data is accumulated and stored in a database and then converted into a 3D surface model with texture mapping using modules M4A, M4B and M4C. The annotation user 92 then annotates on the 3D model for ore grading and geological assessment using module M11.

The system is either commanded by the operator at or automatically looks for and detects existing survey stations 86, and uses the integrated range finder 24 to back-sight them to locate the camera 12 relative to the survey stations 86. The 3D model and the associated geological assessment (M4E) are then transformed into the mine coordinates based on the known location of the survey stations.

This localization step can take place before or after the 3D model creation. Measurements with the integrated rangefinder are more accurate than equivalent measurements with stereo system, which allows for better localization. Once the 3D model is transformed into the mine coordinates, it can be exported (module M12) into mine management software 94 such as Vulcan or Datamine, at the appropriate location of the overall mine map.

This 3D model creation and localization procedure is carried out repeatedly as the mine advances and the photo-realistic 3D models for each mine face are registered together to allow geologists to assess and predict the ore distribution in the mine. The advancing mine faces are labeled as 87, 88 and 89 in FIG. 8.

The method and apparatus for producing 3D models of mine environments disclosed herein is very advantageous because of the capability to create photo-realistic 3D models from mobile stereo cameras for mine cavities and faces, and the ability to register these 3D models in mine map automatically by back-sighting existing survey stations.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A method of producing a three-dimensional (3D) model of an environment, comprising the steps of:
    a) acquiring a first and second plurality of successive stereo images of an environment from at least one of a plurality of stereo cameras which are moving with respect to the environment, the at least one stereo camera having at least two individual image capture means where there is an overlap between images captured by said at least two individual image capture means;
    b) for each image of said first plurality of successive stereo images, detecting features in the stereo images and computing a 3D position and descriptor for each detected feature, and storing said 3D position and said descriptor as a 3D feature in a database;
    c) for each image of said first plurality of successive stereo images, computing relative motion of the at least one stereo camera with respect to the environment by matching the detected features in the stereo images with said 3D features stored in the database using descriptors of said 3D features;
    d) for each image of said second plurality of successive stereo images, computing dense 3D data sets, representative of the environment from the at least one or another of said plurality of stereo cameras;

e) for each image of said second plurality of successive stereo images, transforming the computed dense 3D data from step d) into a selected coordinate frame of reference using the computed relative motion from step c) to give transformed dense 3D data in the selected coordinate frame of reference; and f) storing the transformed dense 3D data for each image of said second plurality of successive stereo images and producing a 3D model of the environment from the stored transformed dense 3D data.

2. The method according to claim 1 wherein said at least one stereo includes first and second stereo cameras, wherein said first plurality of stereo images is acquired by said first stereo camera, wherein said second plurality of stereo images is acquired by said second stereo camera.

3. The method according to claim 2 wherein each successive image of said first plurality of stereo images at least partially overlaps with a preceding image in said first plurality of stereo images.

4. The method according to claim 3 wherein said first stereo camera is in a fixed spatial relationship to said second stereo camera.

5. The method according to claim 4 wherein said acquiring step comprises calculating a time stamp for each image of said first and second plurality of stereo images, and wherein said transforming step comprises comparing time stamps from said first plurality of stereo images to time stamps from said second plurality of stereo images.

6. The method according to claim 4 wherein said first and second stereo cameras acquire said stereo images in a synchronized manner such that each stereo image in said first plurality of stereo images has a corresponding stereo image in said second plurality of stereo images, and wherein said transforming step comprises transforming the computed dense 3D data from said corresponding stereo image from said second plurality of stereo images in step d) into a selected coordinate frame of reference using the computed relative motion from said stereo image from said first plurality of stereo images in step c) to give transformed dense 3D data in the selected coordinate frame of reference.

7. The method according to claim 1 wherein said second plurality of stereo images comprises fewer stereo images than said first plurality of stereo images.

8. The method according to claim 1 further comprising the step of projecting a pattern of dots onto said environment prior to acquiring each image of said second plurality of stereo images.

9. The method according to claim 1 further comprising the steps of acquiring additional data from an additional sensor, and augmenting said 3D model with said additional data.

10. The method according to claim 9 wherein said 3D model is one or combination of surface mesh, point cloud and 3D shapes.

11. The method according to claim 10 wherein combining said 3D model with said additional data comprises texturing or linking said 3D model with said additional data.

12. The method according to claim 11 wherein said additional data is selected from the group consisting of images obtained in the visible and outside visible parts of the light spectrum.

13. An apparatus for producing a three-dimensional (3D) model of an environment, comprising:

a) at least one stereo camera of a plurality of stereo cameras for acquiring a first and second plurality of successive stereo images of an environment which are moving with respect to the environment, the at least one stereo camera having at least two individual image capture means where there is an overlap between images captured by said at least two individual image capture means;

b) processing means programmed with instructions for
 i) detecting, for each image of said first plurality of successive stereo images, features in the stereo images and computing a 3D position and descriptor for each detected feature, and storing said 3D position and said descriptor as a 3D feature in a database;
 ii) for each image of said first plurality of successive stereo images, computing relative motion of the at least one stereo camera with respect to the environment by matching the detected features in the stereo images with said 3D features stored in the database using descriptors of said 3D features;
 iii) for each image of said second plurality of successive stereo images, computing dense 3D data sets, representative of the environment from the at least one or another of said plurality of stereo cameras;
 iv) for each image of said second plurality of successive stereo images, transforming the computed dense 3D data from step b iii) into a selected coordinate frame of reference using the computed relative motion from step b ii) to give transformed dense 3D data in the selected coordinate frame of reference; and
 v) storing the transformed dense 3D data for each image of said second plurality of successive stereo images and producing a 3D model of the environment from the stored transformed dense 3D data.

14. The apparatus according to claim 13 wherein said at least one stereo includes first and second stereo cameras, wherein said first plurality of stereo images is acquired by said first stereo camera, wherein said second plurality of stereo images is acquired by said second stereo camera.

15. The apparatus according to claim 14 wherein said first and second stereo cameras are configured such that each successive image of said first plurality of stereo images at least partially overlaps with a preceding image in said first plurality of stereo images.

16. The apparatus according to claim 15 wherein said first stereo camera is in a fixed spatial relationship to said second stereo camera.

17. The apparatus according to claim 16 wherein said processing means is programmed with instructions for calculating a time stamp for each image of said first and second plurality of stereo images, and wherein said processing means is programmed with instructions for comparing time stamps from said first plurality of stereo images to time stamps from said second plurality of stereo images.

18. The apparatus according to claim 16 wherein said first and second stereo cameras are configured to acquire said stereo images in a synchronized manner such that each stereo image in said first plurality of stereo images has a corresponding stereo image in said second plurality of stereo images, and wherein said processing means is programmed to transform the computed dense 3D data from said corresponding stereo image from said second plurality of stereo images in iv) into a selected coordinate frame of reference using the computed relative motion from said stereo image from said first plurality of stereo images in ii) to give transformed dense 3D data in the selected coordinate frame of reference.

19. The apparatus according to claim 13 further including a light pattern projector for the step of projecting a pattern of dots onto said environment prior to acquiring each image of said second plurality of stereo images.

20. The apparatus according to claim 13 further including an additional sensor for acquiring additional data from an additional sensor, and wherein the processing means is programmed with instructions to augment said 3D model with said additional data.

21. The apparatus according to claim 20 wherein said 3D model is one or combination of surface mesh, point cloud and 3D shapes.

22. The apparatus according to claim 21 wherein combining said 3D model with said additional data comprises texturing or linking said 3D model with said additional data.

23. The apparatus according to claim 22 wherein said additional data is selected from the group consisting of images obtained in the visible and outside visible parts of the light spectrum.

24. A method of producing a three-dimensional (3D) model of an underground environment, comprising the steps of:
   a) acquiring 3D information of an underground environment from at least one range sensing device;
   b) producing a 3D surface model of the underground environment from the acquired 3D information suitable for visualization, analysis or post-processing;
   c) acquiring an image of said underground environment from a camera;
   d) texturing the 3D surface model with said image;
   e) locating the range sensing device by back-sighting to at least two existing survey stations located in the underground environment using a second range sensing device in a fixed relationship to said first range sensing device; and
   f) based on the position information from step e, transforming the 3D model of the underground mine to a map of the underground environment in a coordinate frame of reference of the underground environment.

25. The method according to claim 24 further including the step of annotating the 3D surface model.

26. The method according to claim 25 wherein annotating the 3D surface model comprises annotating for ore grading and geological assessment.

27. The method according to claim 24 wherein said camera and said first range sensing device are combined in a single device.

28. The method according to claim 27 wherein said single device is a stereo camera.

29. An apparatus for producing a three-dimensional (3D) model of an underground environment, comprising:
   a) at least a first range sensing device for acquiring 3D information of an underground environment; and
   b) processing means programmed with instructions for
      i) producing a 3D surface model of the underground environment from the acquired 3D information suitable for visualization, analysis or post-processing;
      ii) acquiring an image of said underground environment from a camera;
      iii) texturing the 3D surface model with said image;
      iv) locating the range sensing device by back-sighting to at least two existing survey stations located in the underground environment using a second range sensing device in a fixed relationship to said first range sensing device; and
      v) based on the position information from iv), transforming the 3D model of the underground mine to a map of the underground environment in a coordinate frame of reference of the underground environment.

30. The apparatus according to claim 29 wherein the processing means is programmed with instructions for annotating the 3D surface model.

31. The apparatus according to claim 30 wherein annotating the 3D surface model comprises annotating for ore grading and geological assessment.

32. The apparatus according to claim 29 wherein said camera and said first range sensing device are combined in a single device.

33. The apparatus according to claim 32 wherein said single device is a stereo camera.

\* \* \* \* \*